United States Patent [19]

Zuckerman et al.

[11] Patent Number: 5,549,889
[45] Date of Patent: Aug. 27, 1996

[54] NEMATOCIDAL AND FUNGICIDAL *STREPTOMYCES DICKLOWII* BIOPESTICIDE

[75] Inventors: Bert M. Zuckerman, Amherst; M. B. Dicklow, South Deerfield, both of Mass.; Nahum Marban-Mendoza, Turrialba, Costa Rica

[73] Assignee: Research Corporation Technologies, Inc., Tucson, Ariz.

[21] Appl. No.: 74,877

[22] PCT Filed: Mar. 5, 1993

[86] PCT No.: PCT/US93/02065

§ 371 Date: Jun. 11, 1993

§ 102(e) Date: Jun. 11, 1993

[87] PCT Pub. No.: WO93/18135

PCT Pub. Date: Sep. 16, 1993

Related U.S. Application Data

[63] Continuation-in-part of Ser. No. 850,627, Mar. 13, 1992, abandoned.

[51] Int. Cl.$^6$ ............... C12N 1/20; A01N 63/00
[52] U.S. Cl. ............... 424/93.43; 435/253.5; 435/886
[58] Field of Search ............... 424/93 G, 93.43; 435/252.35, 886, 253.5

[56] References Cited

U.S. PATENT DOCUMENTS

| | | | |
|---|---|---|---|
| 3,984,564 | 10/1976 | Aoki et al. | 424/274 |
| 4,199,569 | 4/1980 | Chabola et al. | 424/180 |
| 4,534,965 | 8/1985 | Brown et al. | 424/93 |
| 5,279,829 | 1/1994 | Bortolo et al. | 424/122 |
| 5,401,709 | 3/1995 | Andrillo et al. | 504/117 |
| 5,403,584 | 4/1995 | Crawford et al. | 424/93.43 |

FOREIGN PATENT DOCUMENTS

| | | |
|---|---|---|
| 0170006A3 | 5/1986 | European Pat. Off. |
| 2524486 | 7/1983 | France . |
| 2122089 | 1/1984 | United Kingdom . |
| WO92/01038 | 1/1992 | WIPO . |

OTHER PUBLICATIONS

Burg et al (1979) Antimicrobiol agents and Chemotherapy, 15(3), pp. 361–367.
Putter et al (1981) Experimental, 37, pp. 963–964.
Wright et al (1983) Ann appl Biol, 103, pp. 465–470.
Dicklow et al., (1993) *Journal of Chemical Ecology:* 19, pp:159–173.
Zuckerman et al., (1989) *Journal of Chemical Ecology:* 15, No. 6, pp:1947–1956.

*Primary Examiner*—Marian C. Knode
*Assistant Examiner*—Kristin Larson
*Attorney, Agent, or Firm*—Scully, Scott, Murphy & Presser

[57] ABSTRACT

The present invention relates to a newly discovered Streptomyces species, *Streptomyces dicklowii*, which exhibits nematocidal and fungicidal activity in agricultural and horticultural settings. *S. dicklowii* can be used as a biocontrol agent in the treatment and prevention of nematode and/or fungal infection in plants, and particularly in commercially important crop plants.

36 Claims, 6 Drawing Sheets

NEMATOCIDAL AND FUNGICIDAL *STREPTOMYCES DICKLOWII* BIOPESTICIDE

This is a 371 of PCT/US93/02065, filed Mar. 5, 1993, and a contniuation-in-part of U.S. patent application Ser. No. 07/850,627, now abandoned, filed Mar. 13, 1992.

FIELD OF THE INVENTION

The present invention relates to a newly discovered Streptomyces species, Streptomyces dicklowii, which exhibits nematocidal and fungicidal activity in agricultural and horticultural settings. According to the present invention *S. dicklowii* can also inhibit the reproduction of nematodes. *S. dicklowii* and media from *S. dicklowii* cultures can be used as biocontrol agents in the treatment and prevention of nematode and fungal infection in plants, and particularly in commercially important crop plants.

BACKGROUND OF THE INVENTION

Biopesticides are increasingly finding use in agricultural and horticultural settings for pest control. The potential benefit of biopesticides, especially relative to chemical pesticides, continues to spur the search for new biocontrol agents. For example, biopesticides create less pollution and environmental hazards than chemical pesticides. Further biopesticides appear to cause less problem with the development of drug resistance in the pathogenic organisms.

One significant agricultural pest amenable to control using biopesticides is the nematode. Nematode damage to crops is estimated to be more than $3 billion per year yet only about $180 million per year is spent in combating nematode diseases. Since chemical pesticide control of nematodes is relatively expensive, it is thus only used on high value crops. Effective biocontrol agents for nematodes, which are generally cheaper to produce than chemical nematocides, thus promise to improve economic yield for a wider variety of crops.

Another major agricultural problem leading to widespread damage in plants is caused by fungal diseases caused by root rotting organisms. Often the best available methods to combat fungal diseases are chemical fungicides or to use fungus resistant plant cultivars. Such methods of disease management often are neither practical nor desirable. Consequently, biopesticides provide another resource for control of fungal diseases.

Accordingly, *S. dicklowii* and culture media from an *S. dicklowii* culture provide a new and effective nematocidal and fungicidal agent for the control of nematodes and fungi that infect plants, especially economically important crop plants. Moreover, the present *S. dicklowii* have been shown to inhibit nematode reproduction and nematode egg-laying.

SUMMARY OF THE INVENTION

The present invention provides *S. dicklowii*, a newly identified species which exhibits nematocidal and fungicidal activity when applied to plants, particularly commercial crop plants, to the soil or to seeds of such plants. According to the present invention, *S. dicklowii* can further inhibit egg-laying and reproduction in nematodes. *S. dicklowii*, represented by isolate CR-43, provides a means to control and prevent nematode and fungal diseases in plants, particularly fungal root diseases. *S. dicklowii* is thus useful as a biopesticide with many advantages relative to chemical pesticides, especially with respect to environmental effectiveness and cost-effectiveness. A method of using *S. dicklowii* or culture media from a *S. dicklowii* culture to control and prevent nematode or fungal diseases in plants is also provided.

Another aspect of the present invention relates to a biological control agent which is a composition containing an amount of *S. dicklowii* effective to treat a nematode or fungal disease together with an agriculturally acceptable carrier.

DETAILED DESCRIPTION OF THE INVENTION

Figure 1A:
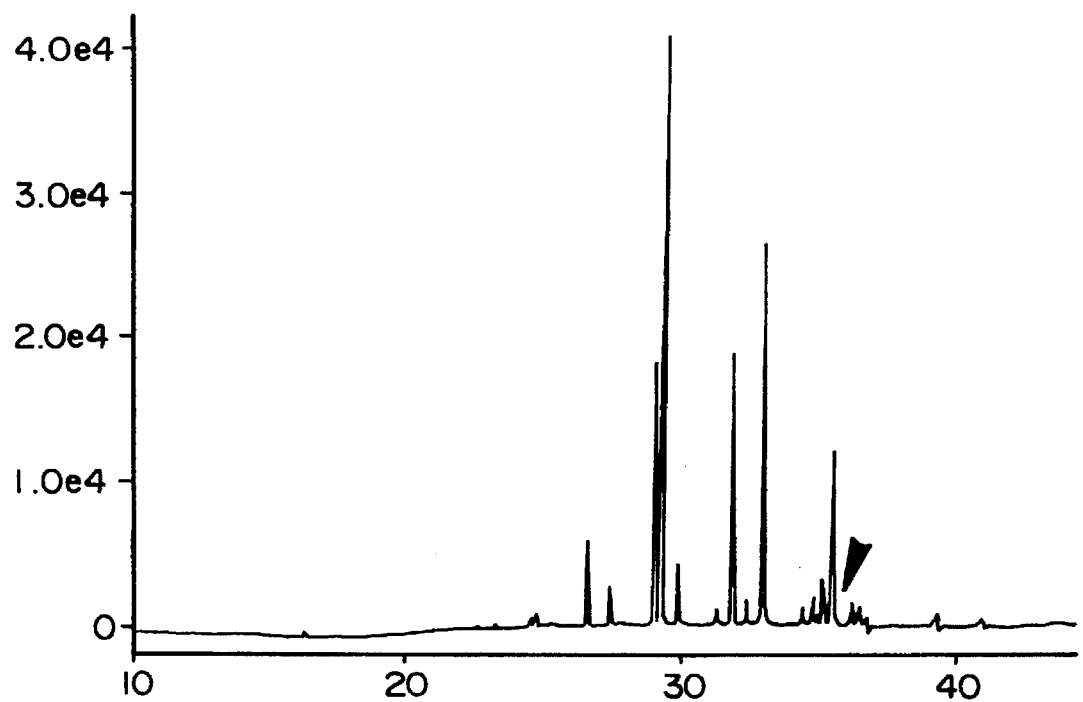
FIG. 1(A) depicts a gas chromatogram of the fatty acid methyl esters present in *S. dicklowii* (CR-43).
Figure 1B:
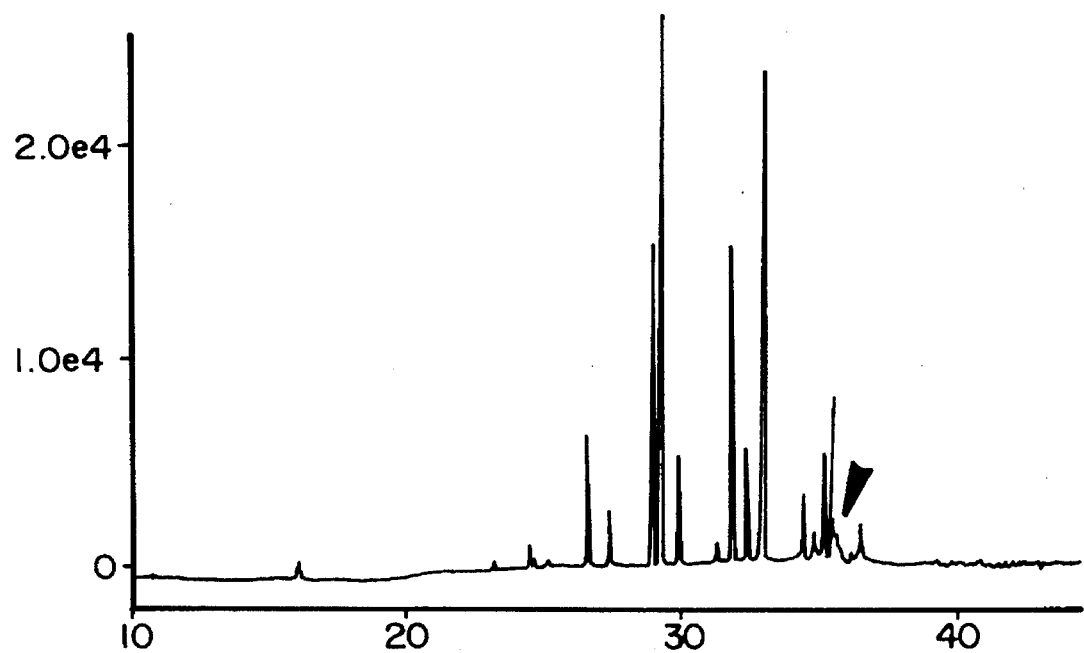
FIG. 1(B) depicts a gas chromatogram of the fatty acid methyl esters present in *S. avermectilis*.
Figure 1C:
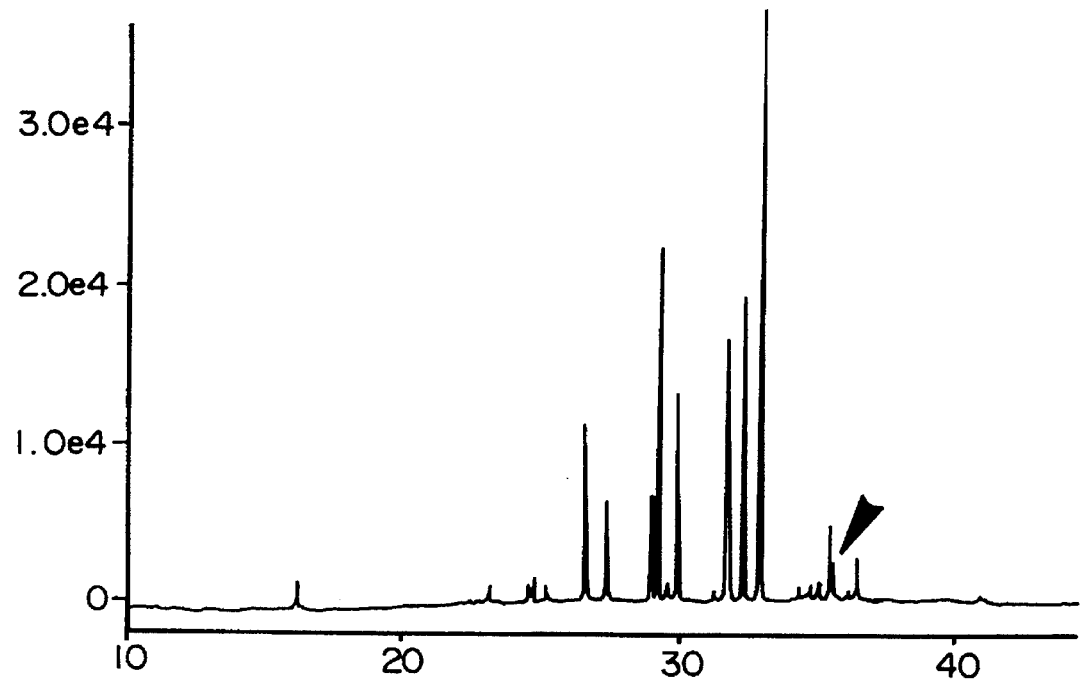
FIG. 1(C) depicts a gas chromatogram of the fatty acid methyl esters present in *S. scabies*.
Figure 1D:
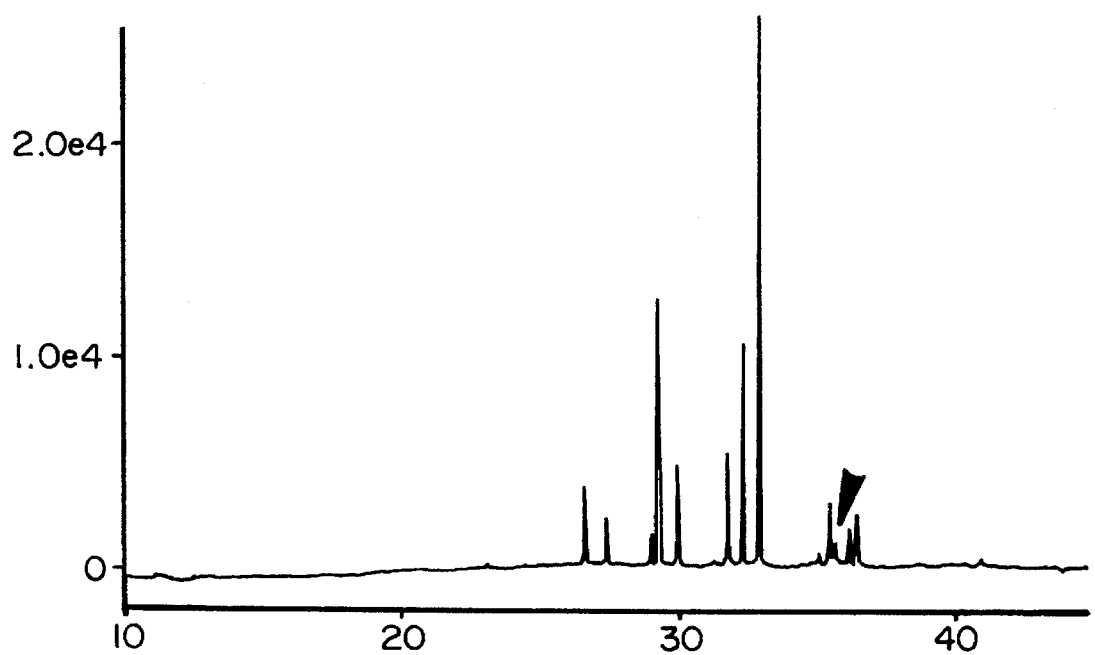
FIG. 1(D) depicts a gas chromatogram of the fatty acid methyl esters present in *S. acetoscabies*.

The present invention relates to *S. dicklowii*, a newly discovered and identified species of Streptomyces, and the cultured medium or spores thereof. *S. dicklowii* or culture media from an *S. dicklowii* culture can be applied directly to seeds, plants or indirectly via the soil to reduce nematode diseases or to prevent nematode-induced crop destruction. Similarly, *S. dicklowii* can be applied as indicated to reduce plant root diseases or to prevent fungus-induced crop destruction. *S. dicklowii*, as represented by strain CR-43, is provided in pure cultures or formulated as a biological control agent for treatment and prevention of nematode and fungal diseases. For example, *S. dicklowii* of the present invention can be isolated from nematode suppressive soils in Costa Rica.

*S. dicklowii* exhibits anti-nematodal properties in vitro and in vivo, for example, in *Caenorhabditis elegans* and *Meloidogyne incognita* Race #3 (nematocidal and reproduction inhibition), *Pratylenchus penetrans* and *Rotylenchulus reniformis*. *S. dicklowii* also displays anti-fungal characteristics against Rhizoctonia spp., Fusarium spp., and Pythium spp. (antibiosis). Sterile culture filtrates retain these effects, although to a lesser degree.

With respect to morphological characteristics, *S. dicklowii* produces aerial mycelium in a gray color series, best described as gray brown. The substrate mycelium is light yellow on yeast extract-malt extract agar (ISP-2), glycerol asparagine agar (ISP-5) and N-Z amine agar with soluble starch and glucose (ATCC medium 172). A yellow diffusible pigment is produced on yeast extract-malt extract agar, glycerol asparagine agar, and N-Z amine agar with soluble starch and glucose. No distinctive pigments are produced on oatmeal agar (ISP- 3) or inorganic starch agar (ISP-4).

*S. dicklowii* produces tightly coiled spiral spore chains. After 14 days the number of conidia per aerial hypha is ten to fifty on all media tested. Conidia are round to slightly elongated and range in size from 1–2 microns.

With respect to physiological characteristics, *S. dicklowii* utilizes D-fructose, glucose, D-mannitol, D-xylose, salicin and galactose. It does not utilize arabinose, raffinose, rhamnose, or sucrose. Acid production in Norcardia Purple broth is positive for cellobiose, glucose, glycerol, maltose, galactose, mannitol, and xylose; and negative for arabinose, fructose, lactose and sucrose. No melanin is produced on peptone-yeast extract-iron agar (ISP-6) or tyrosine agar (ISP-7).

*S. dicklowii* grows well at pH values as low as 4.0 and not at all in the presence of salt (NaCl). It is sensitive to phenol (0.1%), thallium (100 µg/ml) and sodium azide (100 µg/ml); but not to crystal violet (1 µg/ml). *S. dicklowii* grows unchecked in the presence of penicillin (10 IU/ml), but is severely inhibited by the presence of streptomycin (20 µg/ml).

A detailed comparison of the characteristics of *S. dicklowii* and several other Streptomyces spp. is given in Table 1. *S. dicklowii* differs from *S. scabies* and *S. acidiscabies* in several important respects including carbon utilization pattern, melanin production, and morphological characteristics. It also differs from *S. griseus* and *S. sampsonii* as shown in Table 1.

TABLE 1

Characteristics of *S. dicklowii* and other Streptomyces species

| Characteristic | *S. scabies*[a] | *S. sampsonii*[a] | *S. griseus*[a] | *S. dicklowii* |
|---|---|---|---|---|
| Spore Color | Grey | Grey | Grey | Grey-brown |
| Chain morphology | Spiral | Recti- | Recti- | Spiral |
| Spore ornamentation | Smooth | flexous Smooth | flexous Smooth | Smooth |
| Melanin on tyrosine agar | +[b] | — | — | — |
| Pigment on Peptone-Yeast-Extract-Iron Agar | + | — | — | — |
| Carbon Usage | | | | |
| Arabinose | + | + | + | — |
| D-fructose | + | + | + | + |
| D-glucose | + | + | + | + |
| D-mannitol | + | + | + | + |
| Raffinose | + | — | — | — |
| Rhamnose | + | — | — | — |
| Sucrose | + | — | + | — |
| D-xylose | + | + | + | + |
| Salicin | + | + | + | + |
| Nitrogen Usage | | | | |
| L-hydroxyproline | + | — | + | ND |
| L-methionine | + | + | — | ND |
| Minimum growth pH | 5.6 | 5.3 | 5.5 | <4.0 |
| Growth with: | | | | |
| 5% NaCl | + | + | + | — |
| 6% NaCl | + | + | + | — |
| 7% NaCl | — | + | + | — |
| 100 µg NaN₃ | — | — | — | — |
| 1 µg Crystal Violet | — | — | — | + |
| Tellurite (100 µg/ml) | + | + | + | ND |
| Thallium (100 µg/ml) | — | — | + | — |
| Phenol (0.1%) | — | + | + | — |
| Penicillin (10 IU/ml) | — | + | + | + |
| Oleandomycin (100 µg/ml) | — | + | + | ND |
| Streptomycin (20 µg/ml) | — | + | + | — |

[a]The characteristics of these strains are taken from Lambert et al. (1989) Int. J. Sys. Bact. 39:387–392.
[b]+, Positive reaction; —, negative reaction; ND, Not determined.

Direct comparison of the cellular fatty acids present in *S. dicklowii* indicates that *S. dicklowii* contains different types and amounts of fatty acids than other Streptomyces species, e.g. *S. avermectilis*, *S. scabies* and *S. acetoscabies*. In particular, *S. dicklowii* does not have at least one fatty acid which is present in *S. avermectilis*, *S. scabies* and *S. acetoscabies*. *S. dicklowii* also has different amounts of at least two fatty acids than either *S. scabies* or *S. acetoscabies* and a different amount of at least one fatty acid than *S. avermectilis*.

To identify *S. dicklowii*, a candidate strain is tested in accordance with the methods set forth by the International Streptomyces Project (ISP). These tests include carbon source utilization, cultural observation for 14 days using ISP media 2 to 7 and ATCC medium 172, pigment production, color, morphology, pH sensitivity and antibiotic sensitivity using the methods recommended by Shirling et al. (1966a) *Int. J. Sys. Bacteriol.* 16:313–340. Antibiotics are selected and tested to differentiate among Streptomyces spp. as described by Lambert et al. (1989) *Int. J. Sys. Bacteriol.* 39:387–392. *S. dicklowii* of the present invention have the characteristics set forth in Table 1 as well as nematode reproduction-inhibition, nematocidal and fungicidal activity.

A representative *S. dicklowii* strain of the present invention was deposited on Jan. 10, 1992 in accordance with the Budapest Treaty with the American Type Culture Collection (ATCC), 12301 Parklawn Drive, Rockville, Md. 20852. *S. dicklowii* strain CR-43 has been assigned ATCC accession number 55274.

*S. dicklowii* and media from cultured *S. dicklowii* are nematocidal for soil and plant nematodes, including endoparasitic and free-living forms of plant-parasitic nematodes. As used herein nematocidal includes inhibiting nematode egg laying, inhibiting nematode reproduction or growth and killing adult nematodes. Such soil and plant nematodes include species selected from the genera Criconemella, Ditylenchus, Globodera, Helicotylenchus, Heterodera, Longidorus, Meloidogyne, Paratrichodorus, Pratylenchus, Radolpholus, Rotylenchus, Rotylenchulus, Tylenchulus or Xiphinema. More particularly, *S. dicklowii* strains are effective nematocidal agents against *Meloidogyne javanica, Meloidogyne incognita, Meloidogyne arenaria, Meloidogyne hapla, Nacobbus aberrans, Pratylenchus penetrans, Pratylenchus brachyurus, Pratylenchus scribneri, Pratylenchus zeae, Ditylenchus dipsaci, Tylenchulus semipenetrans, Rotylenchulus reniformis, Radolpholus similis* and *Heterodera glycines*.

*S. dicklowii* is neither phytotoxic nor pathogenic for plants. Phytotoxicity to plants by these biocontrol microbes has never been observed after more than 100 greenhouse trials. The assay for phytotoxicity included comparisons of root and top growth of plants treated with these microbes as compared to untreated plants. Analyses included all trials with tomato and strawberry. Field studies on tomato, pepper, plantain, potato and strawberry confirmed these observations. Therefore, none of these organisms are pathogenic to plants, as observed in any of the greenhouse or field trials.

Another embodiment of the present invention is directed to culture media from a cultured *S. dicklowii*. These media include any media which can support the growth of *S. dicklowii* and the secretion of antinematode or anti-fungal agents. After growth of *S. dicklowii*, culture media can be filtered to remove the *S. dicklowii* bacteria or bacteria can be sedimented out of solution. Such a filter can be a 22 μm filter. The culture medium can also be used without actively removing the *S. dicklowii* bacteria. Such culture media can also be concentrated or diluted with an appropriate liquid carrier, e.g. water, a buffer solution, a protein stabilizer or protease inhibitor solution, and the like. These culture media are collected upon secretion of detectable levels of antinematode or anti-fungal factors. For example, media having anti-nematode or anti-fungal properties can be obtained from *S. dicklowii* media cultured for about 2 days to about 7 days, although such factors appear earlier in the growth media and continue to be produced for at least several additional days. Dilutions of *S. dicklowii* culture media which are nematocidally-effective, nematode reproduction-inhibiting or nematode egg-laying inhibiting include undiluted media as well as dilutions of culture medium with up to one volume of liquid carrier. The media from *S. dicklowii* cultures can be stored, e.g. as a liquid or frozen liquid or as a lyophilized powder. Heat treatment and freezing do not significantly alter the antinematodal and antifungal activities of such cultured media.

The *S. dicklowii* strains of this invention can be grown in any conventional growth medium that supports Streptomyces spp. Any liquid or solid media which supports growth of Streptomyces spp., including media conditions which induce sporulation can be used to grow *S. dicklowii*. For example, *S. dicklowii* can be grown on Sporulation Agar (ATCC medium 5), ISP Medium 2 (ATCC medium 196; Difco 0770), Bacto ISP Medium 3 (Difco 0771), Bacto ISP Medium 4 (Difco 0772) and ATCC medium 172. Sporulation Agar per liter of distilled water contains 1.0 g yeast extract, 1.0 g beef extract, 2.0 g tryptose, trace $FeSO_4$, 10.0 g glucose, 15.0 g agar and is adjusted to pH 7.2. This media can be used as broth by omitting the agar and reducing the concentrations of the other ingredients to ⅓ of the given quantities.

ISP medium 2, 3 and 4 are commercially available from Difco. Bacto ISP Medium 4 per liter of distilled water contains 10 g Bacto soluble starch, 1 g $K_2HPO_4$, 1 g $MgSO_4$ USP, 1 g NaCl, 2 g $(NH_4)_2SO_4$, 2 g $CaCO_3$, 0.001 g $FeSO_4.7H_2O$, 0.001 g $MnCl_2.7H_2O$, 0.001 g $ZnSO_4.7H_2O$, and 20 g Bacto agar. ATCC medium 172 per liter of distilled water contains 10 g glucose, 20 g soluble starch, 5 g yeast extract, 5 g N-Z amine type A (Sheffield Chem. Co.), 1 g reagent grade $CaCO_3$ and 15 g agar. These and other media for suitable for growing *S. dicklowii* are described in Shirling et al. (1966b) *Int. J. Sys. Bacteriol.* 19: 501–508. All these media can be used to inhibit nematode and fungus infections after culturing *S. dicklowii* therein.

Typically, sterile media in a flask is inoculated with *S. dicklowii* subculture and grown at 25° C. on a rotary shaker at 200 rpm until the desired culture density is achieved. The growth time varies with the desired culture density. Saturated cultures are usually obtained within 24 h of incubation, however for use as an anti-nematode or anti-fungal reagent, media is preferably collected after secretion of the desired anti-nematode or anti-fungal agents, i.e., after about 2 days. Culture bacterial density is monitored by conventional means, typically by measurement of the optical density of the culture. Viable cells are determined from the colony forming units obtained by plating serial dilutions of the culture on agar plates and counting the number of colonies which form. Alternatively, *S. dicklowii* can be grown on solid agar media by streaking an inoculum across an agar plate with a sterilized wire loop, a sterile toothpick or the like.

In addition, the growth procedures for *S. dicklowii* can readily be scaled up to large fermentors to produce large quantities of pure *S. dicklowii* cultures by methods well known in the art, i.e. batches of 50 to 250 liters or larger. Once grown, whether on large or small scale, the *S. dicklowii* strain can be concentrated by conventional means including centrifugation, filtration, sedimentation and the like.

In order to monitor the presence of *S. dicklowii* on plants, seeds or in the field or soil, a marker gene can be introduced into the strains by conventional means. Suitable marker genes include those genes which encode antibiotic resistance such as rifampicin. Markers can be introduced by plasmids, episomes, bacteriophages and the like and can integrate into the chromosome or reside independently in the cell.

Another aspect of the invention provides derivatives or mutants of *S. dicklowii* strains which retain nematocidal and fungicidal activity. Moreover, this invention is also directed to derivatives or mutants of *S. dicklowii* having either nematocidal or fungicidal activity, i.e. having one or the other property but not both. Similarly the present invention is directed to derivatives or mutants of *S. dicklowii* which have only reproduction- or egg-laying-inhibiting activity and, e.g. have little or no anti-growth activity against nematodes. Such mutants can be made by genetic manipulations, including selection and screening procedures, which are well known in the art. For example, auxotrophies can be introduced into or selected for in the subject *S. dicklowii* strains. To identify an *S. dicklowii* mutant which retains nematocidal activity but has lost fungicidal activity, the parent strain can be analyzed to determine the genetic loci which encode each activity. Similarly, *S. dicklowii* mutants can be screened for strains which have only nematode reproduction-inhibiting or nematode egg-laying inhibiting activity. Once identified these loci can be removed separately from the parent strain using standard genetic methods, e.g. transduction.

Another aspect of this invention is directed to a method of controlling or preventing nematode diseases, in plants and particularly in commercial crops using *S. dicklowii*, and preferably *S. dicklowii* strain CR-43. To treat nematode diseases in accordance with the present method involves contacting the soil, or the soil surrounding a plant, or seeds with a nematocidally-effective amount of at least one *S. dicklowii* strain, and preferably strain CR-43. Such treatments include pre-emergence or post-emergence treatment of the plant. In a preferred embodiment, single or multiple strains of *S. dicklowii* can be employed. Similarly, the vegetative mycelium, spores (conidia) or a combination thereof of *S. dicklowii* can be used in treating nematode diseases.

In another embodiment the present invention provides a method for inhibiting nematode reproduction by contacting the nematode with a reproduction-inhibiting amount of at least one *Streptomyces dicklowii* strain or cultured media from at least one *Streptomyces dicklowii* strain. Similarly the present invention is directed to a method for inhibiting nematode egg laying by contacting a female nematode with an egg laying inhibiting effective amount of at least one *Streptomyces dicklowii* strain or a cultured medium from at least one *Streptomyces dicklowii* strain.

In another embodiment the present invention is directed to a method for controlling or preventing diseases caused by nematodes which includes contacting a soil, a plant or a seed with a nematocidally-effective, reproduction-inhibiting or egg-laying inhibiting amount of a culture medium from an *S. dicklowii* strain.

As used herein "controlling or preventing" or "treating" nematode diseases includes suppression of existing nematode populations in the soils or on plants as well as the prophylactic application of the *S. dicklowii* biopesticide to prevent nematode populations from becoming established in the soil or on the plants. In particular, controlling nematode diseases relates to suppression of existing nematode populations while preventing nematode diseases relates to prophylactic application of *S. dicklowii* or its cultured media. For example, *S. dicklowii* and cultured media which have contained this species can be used to inhibit nematode egg-laying. Therefore, treatment of soils or plants with *S. dicklowii* or cultured media therefrom can prevent nematode populations from becoming established in such soils or plants.

Control of nematode diseases by *S. dicklowii* can be monitored by examining plants for the frequency of symptoms indicating nematode infestation and by counting the number of nematodes present in the soil or on the roots, leaves or stems of plants. Symptoms of nematode infestation include root-knot, wilt, galls, root lesions and the like. Nematode population estimates can be obtained by using a combined sieving and Baermann funnel extraction as in Hooper (1986 Extraction of free-living stages from soil, in J. F. Southey (ed.) *Laboratory Methods for Work with Plant and soil Nematodes.* Ministry of Agriculture, Fisheries and Food Reference Book 402).

Plants which can be treated in accordance with this method include field crops, vegetables, ornamentals and fruit crops. Preferred commercial crops which can be treated to control or prevent nematode diseases include tomato, pepper, strawberry, oranges, pineapple, cotton, plaintain, banana, coffee, soybean, rice, fruit trees and the like. All of these crops are susceptible to severe damage from nematode attack.

The nematodes treatable with *S. dicklowii* can cause root-knot, wilt, galls, root lesions and the like.

Among the nematode diseases preferably treatable with *S. dicklowii* are root knot nematodes on vegetables and fruit trees in the tropics, semitropics and temperate zones, *Radopholus similis* on banana, plantain, pepper and citrus, *Heterodera glycines* on soybean, and *Pratylenchus penetrans* on many temperate zone crops. Hence, the present method can be used to control or prevent such nematode diseases caused in plants by plant-parasitic nematode species selected from the genera Criconemella, Ditylenchus, Globodera, Helicotylenchus, Heterodera, Longidorus, Meloidogyne, Paratrichodorus, pratylenchus, Radolpholus, Rotylenchus, Rotylenchulus, Tylenchulus or Xiphinema. Particularly, nematode species susceptible to treatment by this method with *S. dicklowii* include *M. javanica, M. incognita, M. arenaria, M hapla, N. aberrans, P. penetrans, P. brachyurus, P. scribneri, P. zeae, D. dipsaci, T. semipenetrans, R. reniformis, H. glycines* and *R. similis*.

Preferably, the plants or seeds of the crops are treated pre-emergence or post-emergence with a nematocidally-effective amount of *S. dicklowii*. The preferred *S. dicklowii* strain is CR-43 designated ATCC 55274. Treatments include formulations having either or both the vegetative mycelium and the spores of *S. dicklowii*.

The term "nematocidally-effective" amount is defined herein to be the population of the *S. dicklowii* inoculum or the amount of media from a *S. dicklowii* culture required to reduce the pathological effects of the nematode pathogens and to obtain the desired population of the *S. dicklowii* strains in the soil and/or on the plant. The reduction of pathological effects can be measured by conventional means known in the art and can include such means as reduction of the number of nematodes per plant, increased crop yield, reduction of galling (e.g. as observed in pepper plants), the reduction of fungus infection of roots (as observed in strawberry black root rot infected plants) and the like.

The term "reproduction-inhibiting" amount is defined herein to be the population of the *S. dicklowii* inoculum or the amount of *S. dicklowii* culture medium which is sufficient to reduce normal nematode reproduction. For example, an undiluted *S. dicklowii* medium or a *S. dicklowii* medium which has been diluted by addition of up to one volume of liquid carrier can inhibit normal nematode reproduction. Such an amount can also ameliorate symptoms of nematode infestation in plants. This amount can decrease the number of newly hatched nematodes by, for example, up to about 95% or more.

The term "egg laying-inhibiting" amount is defined herein to be the population of the *S. dicklowii* inoculum or the amount of *S. dicklowii* culture medium which is sufficient to reduce the normal number of eggs laid by a female nematode. Such "egg-laying-inhibiting" media can decrease the number of nematode eggs laid by, for example, up to about 95% or more. This amount also significantly reduces symptoms of nematode infestation in plants.

To ascertain whether an amount of *S. dicklowii* inoculum or culture medium is sufficient to reduce nematode reproduction or egg laying, the number of nematodes present in the soil or on the plant can be determined or the symptoms of nematode infestation can be monitored. The number of nematodes in soil or on plants can be determined by the method of Southey (1986 *Laboratory Methods for Work with Plant and Soil Nematodes,* Ministry of Agriculture, Fisheries and Food Reference Book 402). Symptoms of nematode infestations include root knot, wilt, galls, root lesions and the like. A reproduction-inhibiting or egg-laying inhibiting amount of *S. dicklowii* is an inoculum of *S. dicklowii* sufficient to provide about $10^3$ to $10^8$ colony forming units per gram of soil. A reproduction-inhibiting or egg-laying inhibiting amount of *S. dicklowii* culture medium can be a 2–7 day culture medium which can be diluted with up to one volume of liquid carrier.

Another aspect of this invention is directed to a method of controlling or preventing fungal diseases in plants, especially root rot, damping-off, root galling and the like. In particular, the present method is preferably used to treat commercial plant crops using *S. dicklowii,* and preferably *S. dicklowii* strain CR-43. To treat fungal diseases in accordance with the present method involves contacting the fungi in the soil or in the soil surrounding a plant or on a plant by preemergence or post-emergence treatment of said plant or contacting a seed with a fungicidally-effective amount of at least one *S. dicklowii* strain, and preferably strain CR-43. In a preferred embodiment, single or multiple strains of *S. dicklowii* can be employed. Similarly, the vegetative cells (mycelium), spores (conidia) or a combination thereof of *S. dicklowii* can be used in, treating fungal diseases.

As used herein "controlling or preventing" or "treating" fungal diseases includes suppression of existing fungus populations in the soils or on plants as well as the prophylactic application of the *S. dicklowii* biopesticide to prevent fungus populations from becoming established in the soil or on the plants. In particular, controlling fungal diseases relates to suppression of existing fungus populations while preventing fungal diseases relates to prophylactic application of *S. dicklowii.*

Plants which can be treated in accordance with this method include any which are susceptible to fungal root diseases, and are preferably field crops, vegetables, ornamentals and fruit crops.

Preferred commercial crops which can be treated to control or prevent fungal diseases include tomato, strawberry, soybeans, plantain, banana, coffee, pepper and the like.

Hence, the present method can be used to control or prevent fungal diseases caused in plants by fungi from the genera Rhizoctonia, Pythium and Fusarium, and more particularly those diseases caused by *Rhizoctonia solani* on soybeans, *Rhizoctonia fragariae* on Strawberry, Pythium spp. causing damping-off and root rot of greenhouse and field crops, and Fusarium wilt of tomatoes and other crops.

Preferably, the plants or seeds of the crops are treated pre-emergence or post-emergence with a fungicidally-effective amount of *S. dicklowii.* The preferred *S. dicklowii* strain is CR-43 designated ATCC 55274. Treatments include formulations having either or both the vegetative mycelium and the spores of *S. dicklowii.*

The term "fungicidally-effective" amount is defined herein to be the population of the *S. dicklowii* inoculum required to reduce the pathological effects of the fungus and thereby to obtain the desired population of *S. dicklowii* in the soil or on the plant. The reduction of pathological effects can be measured by conventional means known in the art and can include such means as reduction of the number of fungi per plant, increased crop yield, measures of root size and integrity, reduction in the number of lesions per root, the degree of vascular discoloration and the like.

The following definitions, methods, explanations, terms and conditions apply to both of the above methods.

Treatment on a pre-emergence basis includes treatment of plant seeds from any time prior to implantation up to the appearance of a seedling or plantlet and includes such treatments as coating the seeds with a preparation containing one or more *S. dicklowii* strains. Pre-emergence treatment also includes application of *S. dicklowii,* such as drench, to the soil before planting seeds. Post-emergence treatment then encompasses treatment after the seedling or plantlet appears above the soil and includes treatments applied when the plants or plantlets are transplanted such as adding *S. dicklowii* drenches to the plant hole at transplantation, incorporating *S. dicklowii* into fertilizers or other preparations applied during transplantation or treatments applied during plant growth, such as with sprays, dusting, drenches and the like.

The present methods can be used with plants or crops grown in the greenhouse or in the field. An inoculum of one or more *S. dicklowii* strains is used such that colonization in the range of about $10^3$–$10^8$ colony forming units per gram (cfu/g) soil occurs and preferably about $10^4$–$10^7$ cfu/g soil or about $10^5$–$10^6$ cfu/g soil. Culture media from a *S. dicklowii* cultured for at least 2 days is used either undiluted or diluted with carrier, e.g. 1:1, 1:2 or 1:4 (culture medium:carrier). The inoculum or cultured media can be applied directly to the seeds or plants, can be present in the soil before planting or can be distributed, e.g. by spreading, dusting of the like, over the crop or soil where the crop has been planted or is to be planted. Any inoculum or cultured media of one or more *S. dicklowii* strains can be applied, provided that inoculum or cultured media imparts a nematocidally-effective amount, reproduction-inhibiting amount or nematode egg-laying inhibiting amount when treating nematode diseases or a fungicidally-effective amount when treating fungal diseases.

Seeds can be treated by coating with a composition containing *S. dicklowii* or a cultured medium from *S. dicklowii* by dipping the seeds in a liquid or other composition which contains or has contained these microbes, by spraying the liquid on the seeds or applying the liquid to the seeds by any other conventional method known in the art for applying bacterial microbes to seeds.

A further aspect of this invention provides *S. dicklowii* formulated as a biological control agent for control and prevention of nematode or fungal diseases in plants which comprises an amount of at least one *S. dicklowii* strain effective to treat the disease and an agriculturally acceptable carrier therefor. Preferably, the *S. dicklowii* strain is CR-43 (ATCC accession No. 55274). The biological control agent can be formulated with conventional agricultural carriers, such as those typically used with chemical pesticides. Any of the various types of compositions commonly used in applying chemical pesticides can be reformulated with a biopesticide in accordance with the present invention. Such compositions are well known in the art and provided, for example, by Lucas et al. (1985) *Introduction to Plant Diseases,* The AVI Publishing Company, Inc., Westport, Conn., especially Chapters 5–7. Such compositions can include seed coats, fertilizers, peat, prepackaged soil, drenches, dusts, sprays, powders, liquids and the like.

When the biological control agent is formulated as peat, fertilizer, prepackaged soil and the like, the *S. dicklowii* mycelium or spores are grown in broth to the desired quantity, concentrated if necessary, and mixed with peat or soil at the desired inoculum. Optionally this mixture may be cured by well known methods to form a granular composition.

The agriculturally acceptable carriers that can be used to disperse the subject strains on a pre- or post-emergence basis include all those commonly used carriers for dispersing nematocides or fungicides on crops and plants. These carriers include water, clay, talc and other dusting agents. The *S. dicklowii* mycelium or spores in such compositions are present at a level of about $10^3$–$10^8$ cfu/g carrier, especially $10^4$–$10^8$ cfu/g carrier, and more especially $10^5$–$10^6$ cfu/g carrier, provided that the selected concentration is a nematocidally-effective, reproduction-inhibiting, egg laying-inhibiting or fungicidally-effective amount for the composition in accordance with the present invention.

Any of the above biocontrol compositions, e.g. liquids, drenches, powders, peat, soil and the like can have nutrients and fertilizing agents included therein or an appropriate carrier medium such as water, oils or solid bases such as powders, peat, soil, fertilizer, clay, talc or any other dusting agent.

The following examples serve to further illustrate the invention.

EXAMPLE 1

Identification of *S. dicklowii* CR-43

*S. dicklowii* strain CR-43 was isolated from nematode-suppressive soil from Costa Rica as set forth in Zuckerman et al. (1989) *J. Chem. Ecol.* 15: 1947. The following tests were performed to characterize isolate CR-43.

Carbon Source Utilization: These tests were performed according to the methods set forth by the International Streptomyces Project (ISP).

Cultural Observations: Characteristics were recorded after 14 days of incubation using ISP Media 2 to 7 and ATCC Medium 172 and employing methods recommended by Shirling et al.

Pigment Production, Color and Morphology: The production of melanin on tyrosine agar (ISP-7) and peptone-yeast extract-Ion agar (ISP-6) was determined. Spore mass, spore chain morphology, and diffusible pigment colors were described according to Shirling et al. on ISP Media 2 to 9 and ATCC Medium 172.

pH Sensitivity: The minimum pH that allowed growth was determined on ISP Medium 2 (4.0 g yeast extract, 10.0 g malt extract, 4.0 g dextrose, 20.0 g agar per liter distilled water). pH adjustments were made with HCl and KOH.

Antibiotic Activity: The toxicities of antibiotics and other inhibitory compounds were determined on ISP Medium 2. The toxic compounds used were selected from Lambert et al. as compounds chosen for their ability to differentiate species of Streptomycetes.

Media: ISP Medium 2 (ISP-2) is yeast extract-malt extract agar. ISP Medium 3 (ISP-3) is oatmeal agar. ISP Medium 4 (ISP-4) is inorganic starch agar, ISP Medium 5 (ISP-5) is glycerol asparagine agar. ISP Medium 6 (ISP-6) is peptone-yeast extract ion agar. ISP Medium 7 (ISP-7) is tyrosine agar. The formulations of these media is reported in Shirling et al. (1966b). ATCC Medium 172 is N-Z amine with soluble starch and glucose; the formulation thereof is provided in the detailed description.

Fatty Acid Profiles: The fatty acids present in *S. dicklowii* CR-43 were compared to the fatty acids present in three other Streptomyces species, *S. avermectilis, S. scabies* and *S. acetoscabies*. Fatty acids were extracted by the method of Vanniewenhuyze et al. (1987 Chromatographia 23:1850–1855) and esterified to the methyl ester by treatment with 1 ml 5% NaOH in 50% MeOH at 100° C. for 30 min. The fatty acid methyl esters (FAME) were then applied to a Hewlett Packert HP5890 series 2 gas chromatograph. The injected sample consisted of 1 μl exacted FAME in hexane flushed with 1 μl dichloromethane. As depicted in FIGS. 1, *S. dicklowii* CR-43 (FIG. 1A) does not have an elution peak (arrow) at retention time 35.7 min, whereas each of *S. avermectilis* (FIG. 1B), *S. scabies* (FIG. 1C) and *S. acetoscabies* (FIG. 1D) do have an elution peak (arrow) at 35.7 min. Other differences are also apparent between the FAME profile of *S. dicklowii* CR-43 and the FAME profile of the other Streptomyces species. For example, the ratio of FAME concentration at retention time 34.4 min to that at 36.2 min was less than one for *S. dicklowii* CR-43 (FIG. 1A) but greater than one for *S. avermectilis* (FIG. 1B). The ratio of FAME concentration at retention time 29.3 min to that at 32.9 min was greater than one for *S. dicklowii* CR-43 (FIG. 1A) but less than one for both *S. scabies* (FIG. 1C) and *S. acetoscabies*. Similarly, the ratio of FAME concentration at retention time 31.8 min to that at 32.4 min was greater than one for *S. dicklowii* CR-43 (FIG. 1A) but less than one for both *S. scabies* (FIG. 1C) and *S. acetoscabies*.

Results: The characteristics of isolate CR-43 are set forth in Table 1. Based upon the criteria of Bergey's *Manual of Sytemic Bacteriology,* Vol. 4 (1989), CR-43 could not be placed in a described species. Accordingly, CR-43 was designated as the prototype strain for the new species *S. dicklowii.*

EXAMPLE 2

Field Trials

Four replicate plots (20'×10') containing two 20' rows of peppers and two 20' rows of tomatoes were planted for nematode biocontrol studies at the University of Puerto Rico Agricultural Research Station, Isabela, Puerto Rico. Each row contained 20 plants. The experimental area contained a high, natural infection of root-knot nematode, *M. incognita.*

Tomato or pepper plantlets raised in a greenhouse were transplanted into the plots and treated with CR-43, no added CR-43 (control), or NEMACUR® (a commercial chemical nematocide) at a recommended rate. For CR-43-treated plot, the seeds were coated with CR- 43. The seed coat was prepared by growing CR-43 on bran at 25° C. for 7 days, drying and grinding the mix, adding 2 g dried material to 10 ml methyl cellulose to treat 1 g seeds. Coated seeds were dried for 24 h. For drenches, after concentrating the CR-43 inoculum grown in nutrient broth by centrifugation, most of the nutrient broth was removed, the concentrated inoculum was resuspended in water to $1 \times 10^5$ CFU/ml of CR-43 and a 50 ml inoculum drenched on each plant. Controls for both seed coated and drench plants were similarly prepared, but without addition of CR-43. Plants in the control-treated plot, received 50 ml of nutrient broth without CR-43. Plants in the NEMACUR-treated plots received NEMACUR at a recommended rate.

In a similar field trial at the University of Puerto Rico Agricultural Research Station, test pepper seeds were coated with CR-43 as described above whereas untreated control pepper seeds received no CR-43. Seeds were germinated and grown in 2 inch pots to a height of 4–5 inches prior to transplantation. For comparison, some field plots planted with peppers receiving no CR-43 were treated with the commercially available nematicide NEMACUR (15% active ingredient) as prescribed by the supplier.

At maturity the peppers were harvested and cumulative yields were calculated as shown in Tables 2A and 2B. Statistical analyses of results were by Duncan's multiple-range test or by Minitab t tests.

The yield of CR-43 treated peppers was significantly greater than the untreated controls, and only slightly less than the chemically treated plots.

Treatment with CR-43 resulted in a significant reduction in root galling due to the nematode *M. incognita.*

Nematode populations were analyzed from all plots 3 times as follows: (1) prior to the experiment; (2) at the midpoint of the experiment and (3) at the time of first harvest. The duration of the experiment was 3 months. Populations of the reniform nematode, *R. reniformis,* were reduced significantly.

TABLE 2A

Yield of Pepper Treated with CR-43 as a Seed Coat and NEMACUR in a Field Heavily Infested with Root-knot Nematode (*Meloidogyne incognita*). Isabela Expt. Station, Puerto Rico.

| Treatment | Yield (kg pepper/plot)[1] |
| --- | --- |
| None (control) | 11.4[a] |
| CR-43 | 18.5[b] |
| NEMACUR | 19.4[b] |

[1]Figures followed by different letters are significantly different at the 5% level.

TABLE 2B

Yield of Pepper Treated with CR-43 as a Seed Coat or NEMACUR in a Field Heavily Infested with Nematodes. Isabela Expt. Station, Puerto Rico.[a]

| Treatment | Yield (kg pepper/plot)[1] | % Increase in Yield | Fungal Gall Index |
| --- | --- | --- | --- |
| None (control) | 11 ± 2b[c] | — | 2.0 ± 1.2a[d] |
| CR-43 | 18 ± 4a | 62% | 0.7 ± 0.6b |
| NEMACUR | 19 ± 2a | 70% | 0.5 ± 0.4b |

[a]Numbers followed by different letters are significantly different at P = 0.05.
[b]Each treatment was replicated four times.
[c]Means separated by t tests (Minitab).
[d]Means separated by Duncan's multiple range test (SAS).

Significant reductions in nematode-related gall infections (P=0.05) occurred in plots having plants treated with CR-43. Moreover, nematode sampling at 12 weeks indicated an 85% reduction in soil populations of the reniform nematode *R. reniformis* in CR-43 treated plots as compared to untreated controls. Yields were also increased significantly (P=0.05) when CR-43 was employed, approximating yields attained by chemical nematicide treatment.

EXAMPLE 3

Field Trials

Four replicate plots (20'×10') containing 10 tomato or pepper plants per row were planted for nematode biocontrol tests at the University of Puerto Rico Agricultural Research Station, Isabela, Puerto Rico.

The plants were treated with drench as described in Example 2.

From these plots, peppers were harvested three times and tomatoes harvested five times. There were 4 applications of the biocontrol organism CR-43, nutrient broth (control) or NEMACUR as described in Example 2. The results are shown in Table 3A which provides the average yield for tomatoes and peppers as well as the percent yield over the control. Treatment with CR-43 caused a 26% and a 21% yield increase for peppers and tomatoes, respectively, relative to the controls. However, it should be noted that the tomatoes were heavily affected by the fungus Pythium in this experiment. The yield increase could be partially attributed to the anti-fungal efficacy of CR-43 against Pythium. The plots were sampled for nematode populations as in Example 2. Galling by root knot nematode (*M. incognita*) was significantly less in CR-43 treated plants than in control (untreated plants). (Table 3B).

TABLE 3A

Field Experiment on Tomato and Pepper in a Field Naturally Infested with *Meloidogyne incognita*. Isabela Exp. Station, Puerto Rico.

| | Pepper[a] | | Tomato[a] | |
| --- | --- | --- | --- | --- |
| Treatment | (Ave. Yield) Kg | Yield[b] % | (Ave. Yield) Kg | Yield[b] % |
| None | 18.3 | — | 114.8 | — |
| CR-43 | 23.2 | 26 | 139.2 | 21 |
| NEMACUR | 19.4 | 6 | 133.2 | 16 |

[a]Total Number of Plants: Tomato-1760; Pepper-880.
[b]Yield % = increased yield over untreated control.

TABLE 3B

| Pepper Gall Index | |
| --- | --- |
| Treatment | Gall Index[1] |
| None | 2.04 a |
| CR-43 | 0.708b |
| NEMACUR | 0.450b |

[1]Figures followed by different letters are significantly different at the 5% level.

EXAMPLE 4

Field Trials

A field trial on strawberry in 1990–1991 was used to evaluate biocontrol of CR-43 on black root rot, a disease complex caused by the fungus *R. fragariae* and the nematode *P. penetrans*. CR-43 was applied as a drench ($10^5$ CFU/ml) at 50 ml/plant in 3 applications at 4 week intervals starting in June, 1990. There were 25 strawberry plants/plot, 4 replicate plots to which CR-43 was applied, and the same number of plants treated the same way but without CR-43 (control). Thus, the experiment contained 200 plants. Five plants in each plot were destructively sampled for nematodes in the Fall, 1990, and the remaining plants analyzed in the Summer, 1991.

The results showed more than 100% reduction in nematode populations in roots by the Summer, 1991 (Table 4A). There was also a significant reduction in black root rot by the Summer, 1991, showing a reduction of *R. fragariae* infection associated with treatment with CR-43 (Table 4B).

TABLE 4A

Field Trial for Efficacy of CR-43 in Reducing
R. fragariae - P. penetrans
Infestation on Strawberry Plants

| Treatment | # berries/ meter | Yield (g)/ meter | # P. penetrans/g root Fall 1990 | # P. penetrans/g root Summer 1991 |
|---|---|---|---|---|
| None | 200.8 | 455.8 | 192.0 | 82.0 |
| CR-43 | 265.0 | 694.4 | 144.0 | 30.0 |

TABLE 4B

Field Trial for Efficacy of CR-43 in Reducing Black Root Rot of Strawberry Plants

| | Mean weight (g)/ berry | Black root Rot Index[1] F 1990 | Black root Rot Index S 1991 |
|---|---|---|---|
| None | 2.17 | 3.4a | 3.6b |
| CR-43 | 2.57 | 3.4a | 2.7a |

[1]F, fall; S, summer; Figures followed by different letters are significantly different at the 5% level.

EXAMPLE 5

Field Trial: Isabela Exp. Station, Puerto Rico

Nematode biocontrol studies were performed at the University of Puerto Rico Agricultural Research Station, Isabela, Puerto Rico, to determine the efficacy of *S. dicklowii* CR-43 for controlling nematode and fungal infection. The efficacy of CR-43 was also compared with that of a commercially available nematicide, NEMACUR.

CR-43 was applied as a drench as follows. A CR-43 inoculum was grown for five days in 1 liter potato dextrose broth (PDB) then added to 10 liters of PDB and fermented for 24 hr to a final concentration of $1 \times 10^{5-6}$ colony forming units (CFU) per ml. Fermentations were performed in Massachusetts, cultures were then packed on ice and shipped to Puerto Rico by overnight carrier. Prior to shipping CR-43 bacterium were concentrated by centrifugation and the supernatant was removed. In the field, water was added to bring the CR-43 back to a concentration of $1 \times 10^{5-6}$ CFU/per ml. A volume of 50 ml CR-43 bacterial suspension was applied to each plant. During the first 8 weeks of the 12 week experiment, CR-43 was applied four times at two week intervals.

NEMACUR°, a pharmaceutical for killing weeds and vermin, manufactured by Bayer U.K. Ltd. was used as specified by the manufacturer.

Four replicate experiments were performed for each of the untreated control, CR-43 treated and NEMACUR treated plots. Plots consisted of 40 tomato or 40 pepper plants. The total yields of five tomato harvests and five pepper harvests were separately combined in the data provided in Tables 5A and 5B.

Nematode soil populations were sampled when the experiment was initiated, after six weeks and at 53 days (during harvest). Population estimates, including levels of *R. reniformis* were obtained using a combined sieving and Baermann funnel extraction as in Hooper (1986 Extraction of free-living stages from soil, pp. 5–30, in J. F. Southey (ed.) *Laboratory Methods for Work with Plant and soil Nematodes*. Ministry of Agriculture, Fisheries and Food Reference Book 402).

TABLE 5A

Field Experiment on Tomato and Pepper in a Field Naturally Infested with *Meloidogyne incognita*. Isabela Exp. Station, Puerto Rico.

| | Pepper | | Tomato | |
|---|---|---|---|---|
| Treatment[b] | (Ave. Yield) Kg[c] | Yield[b] Increase %[d] | (Ave. Yield) Kg[c] | Yield[b] Increase %[d] |
| None | 18 ± 5 | — | 115 ± 11 | — |
| CR-43 | 23 ± 2 | 26 | 139 ± 17 | 12 |
| NEMACUR | 19 ± 3 | 9 | 133 ± 9 | 11 |

[b]Each treatment was replicated four times.
[c]Means separated by t tests (Minitab).
[d]Yield increase expressed as percent increase over untreated controls.

TABLE 5B

| Tomato Gall Index[a] | |
|---|---|
| Treatment[b] | Gall Index[e] |
| None | 4.3 ± 1.6a |
| NEMACUR | 4.4 ± 1.3a |
| CR-43 | 2.3 ± 1.5b |

[a]Numbers followed by different letters differ at P = 0.05
[b]Each treatment was replicated four times.
[c]Means separated by t tests (Minitab).
[d]Yield increase expressed as percent increase over untreated controls.
[e]Means separated by Duncan's multiple range test (SAS).

These results demonstrate that *S. dicklowii* is particularly effective at increasing crop yields, at reducing the number of nematodes in the soil and at reducing the number of galls caused by nematode infection of plants.

EXAMPLE 6

Greenhouse Trials

Organisms

*Streptomyces dicklowii* CR-43 inoculum for experiments was stored in cryopreservation buffer (Brenner 1974 *Genetics* 77: 71–94) at –80° C. When required for experimentation the organism was grown on potato dextrose agar (PDA) at 25° C. or potato dextrose broth (PDB) at ambient room temperature on a rotary shaker at 100 rpm.

*Meloidogyne incognita* race 3 was obtained from Dr. M. McClure, University of Arizona. Inoculum for experiments consisted of eggs obtained from root-knot-infected tomato roots by the method of Hussey et al. (1973 *Plant Dis. Rep.* 57: 1025–1028).

Methods

Control of nematode *M. incognita*-induced root galling was evaluated in greenhouse trials using three different methods of application: liquid drench, oatmeal culture or seed coat.

Liquid cultures of CR-43 for drench applications were prepared by inoculating 100 µl of cryopreserved CR-43 into 50 ml PDB medium in a 250 ml Erlenmeter flask. The cultures were incubated at ambient room temperature on a rotary shaker at 100 rpm for 7–10 days. A control of PDB medium alone was tested and found non-phytotoxic.

In the drench trial, CR-43 inoculum was added to 1 liter pots containing 1 part sterilized potting soil and 1 part washed sand. A 2- to 3-week old tomato seedling was transplanted to each pot and grown for one week. After one week of growth, 5,000–10,000 *M. incognita* eggs (numbers of eggs did not vary within an experiment but did vary between experiments) were then added to test pots. Control pots, receiving medium and no CR-45, also received the requisite number of *M. incognita* eggs. Experiments were terminated after six weeks. There were five replicates of each treatment type.

Oatmeal cultures were prepared by adding 15 ml sterile distilled water to 25 g autoclaved oatmeal in a 250 ml Erlenmeyer flask and adding a 5 mm plug from a CR-43 PDA culture. Flasks were incubated at 25° C. for 7–10 days, during which period they were shaken by hand once each day to ensure even colonization of the oatmeal. Each greenhouse pot received 25 g CR-43 oatmeal culture. Negative control pots received 25 g of oatmeal culture containing no CR-43 and infected with *M. incognita*. Five replicates of each treatment type were performed.

For seed coats, CR-43 was combined with methyl cellulose and carrier by the method of Townshend et al. (1989 *J. Nematol.* 21:179–183). A control seed coat of methyl cellulose and carrier with no CR-43 demonstrated that such a seed coat was not phytotoxic. Coated seed was planted directly into a mixture of 1 part sterile potting soil and 1 part sand in 1 liter pots previously infested with 10,000 eggs of *M. incognita*. At 21 days seedlings were thinned to 1 per pot. The experiment was terminated after 10 weeks. Five replicates were performed of each treatment type.

The degree of galling was evaluated by counting the number (N) of galls on each root system. Statistical analyses of greenhouse data were by ANOVA supplemented by paired t tests (Minitab, Pa.) or by ANOVA and means separated by Duncan's multiple range test (SAS Institute, Inc., Cary, N.C.).

Results

All modes of CR-43 application tested, i.e. liquid drench, oatmeal culture and seed coat, were highly effective for reducing the number of *M. incognita* nematode root galls, in a statistically significant manner (P=0.05; see Table 6).

TABLE 6

Greenhouse Trials for Efficacy of CR-43 in Reducing *M. incognita* (MI) Nematode Root Galls

|  | Number of Galls | Gall Reduction (%) |
|---|---|---|
| Trial 1[b] | | |
| Oat medium + MI | 125 ± 59a | |
| CR-43 + oat medium + MI | 68 ± 36b | 54% |
| Trial 2[c] | | |
| Drench medium (PDB) + MI | 148 ± 20a | |
| CR-43 + medium + MI | 74 ± 16b | 50% |
| Trial 3[c] | | |
| Seed coat + MI | 283 ± 155a | |
| Seed coat + MI + CR-43 | 65 ± 23.5b | 23% |

[a] Each treatment was replicated five times. Numbers followed by different letters differ at P = 0.05.
[b] Means separated by t tests (Minitab).
[c] Means separated by Duncan's multiple range test (SAS).

These results demonstrate that *S. dicklowii* CR-43 is a highly effective nematocidal agent capable of reducing the number of galls resulting from nematodal infection by at least 23% to 54%.

EXAMPLE 7

In Vitro Antifungal Activity of *Streptomyces dicklowii* CR-43

Organisms

*Streptomyces dicklowii* CR-43 inoculum for experiments was stored in cryopreservation buffer (Brenner 1974 *Genetics* 77: 71–94) at –80° C. When required for experimentation the organism was grown on potato dextrose agar (PDA) at 25° C. or potato dextrose broth (PDB) at ambient room temperature on a rotary shaker at 100 rpm.

Pure cultures of *Rhizoctonia solani* and *Pythium aphanidermatum* were supplied by Dr. W. Manning, Department of Plant Pathology, University of Massachusetts, Amherst.

Methods

Four 5 mm plugs of CR-43 on PDA were placed equidistant and 3 cm from the center of a 9 cm Petri plate. A 5 mm plug of the test fungal species was placed in the center of the plate. The activity of CR-43 exometabolites was evaluated against *Rhizoctonia solani* and *Pythium aphanidermatum* by spotting CR-43 culture filtrates and CR-43 exometabolites onto Petri plates at a given distance from the test fungal species. PDA plugs were used as controls. The plates were incubated at 25° C. and observed at 72 hr for zones of inhibition.

Results

Figure 2:
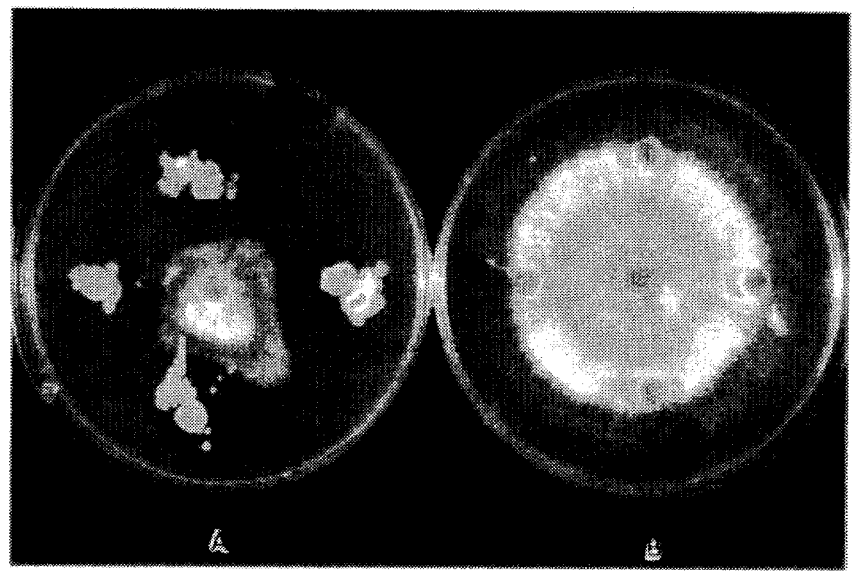
In FIG. 2, petri dish A depicts the growth inhibition of fungus Rhizoctonia solani around agar plugs containing *S. dicklowii* (CR-43), and petri dish B depicts the no growth inhibition of fungus Rhizoctonia solani around agar plug controls which have no *S. dicklowii* (CR-43).

As illustrated in FIG. 2 the presence of CR-43 substantially inhibited the growth of the fungus *Rhizoctonia solani*. In particular little or no *Rhizoctonia solani* grew in the region of *S. dicklowii* CR-43 (FIG. 2A) whereas substantial amounts of *Rhizoctonia solani* grew when no CR-43 was present.

EXAMPLE 8

In Vitro Nematocidal Activity of *Streptomyces dicklowii* CR-43

Organisms

*Streptomyces dicklowii* CR-43 inoculum for experiments was stored in cryopreservation buffer (Brenner 1974 *Genetics* 77: 71–94) at -80° C. When required for experimentation the organism was grown on potato dextrose agar (PDA) at 25° C. or potato dextrose broth (PDB) at ambient room temperature on a rotary shaker at 100 rpm.

*Caenorhabditis elegans* was cultured on liver extract medium as in Sayre et al. (1963 *Exp. Parasitol.* 13: 98–107).

Methods

CR-43 Culture Filtrate (CF): Cultures of *Streptomyces dicklowii* CR-43 were filtered using a sterile 22 μm Acrodisc filter to produce CR-43 culture filtrate (CF). CF was boiled for 5 min and frozen to assess the effect of these manipulations upon the antinematocidal activity of CF.

CF Nematocidal Assays: CF was diluted with liver extract (LE) medium to concentrations of 1:1, 2:1, 4:1 and 8:1 (CF:LE) and these dilutions were placed in microtiter wells. Controls containing PDB and liver extract with no CF were also prepared. Liver extract contains a factor needed for *C. elegans* growth, therefore a separate control for each liver extract concentration was prepared, i.e. such controls consisted of 1:1, 2:1, 4:1 and 8:1 dilutions of PDB with liver extract. Boiled CF and frozen CF were tested in a similar manner.

Fifty age-synchronized second-stage *C. elegans* larvae produced as in Zuckerman et al. (1983 *J. Am. Assoc.* 6:1–4), were added to each well. The plates were sealed with parafilm and held at 22° C. for seven days.

The impact of CF on nematocidal reproduction was assessed by withdrawing three 50 μl aliquots from each well and counting the number of *C. elegans* in each aliquot.

To assess the impact of CF on nematocidal growth, the lengths of five nematodes from each well were measured.

The time required for production of CR-43 anti-nematocidal factor in newly inoculated cultures was determined by growing CR-43 in PDB for 1–7 days and collecting culture filtrate (CF) on each day of culture. Three replicate CR-43 cultures were tested simultaneously in duplicate for each day of culture. The entire experiment was performed twice. To test each CF collected, 50 newly hatched *C. elegans* were added to 2.5 ml CF and the cultures were incubated at 22° C. for seven days. Three 50 μl aliquots were withdrawn for each culture and the number of nematodes were counted.

Results

As illustrated in Table 7, reproduction of *C. elegans* was inhibited at lower concentrations of CF than were needed to inhibit *C. elegans* growth. In particular, at 1:1, 2:1 and 4:1 concentrations of CF:liver extract, *C. elegans* reproduction was inhibited by up to about 95% whereas there was no significant effect upon *C. elegans* growth at these concentrations. However at an 8:1 concentration of CF:liver extract *C. elegans* growth was inhibited by about 36%.

Boiling and freezing CF had little or no effect upon the inhibitory activity of CF against *C. elegans* reproduction.

As illustrated in Table 8, CR-43 nematocidal activity begins to be present in the culture medium after about .2 days of CR-43 culture. Higher levels of CR-43 nematocidal activity are present in culture filtrates after about 3–4 days of incubation. Reproduction of nematodes can be inhibited by up to 96% using 7-day CR-43 culture filtrates.

TABLE 7

Effect of Different Concentrations of CR-43 Culture Filtrate (CF) on *C. elegans* Reproduction and Growth[a]

| Treatment[b] | CF:Liver Extract or PDB:Liver Extract | Reproduction (Number of *C. elegans*)[c] | Growth (Length in μm)[d] |
|---|---|---|---|
| Control (PDB) | 1:1 | 116 ± 33a | 992 ± 20 |
|  | 2:1 | 125 ± 39a | 1,088 ± 14 |
|  | 4:1 | 135 ± 12a | 821 ± 12 |
|  | 8:1 | 59 ± 10a | 624 ± 21 |
| CF | 1:1 | 13 ± 4b | 1,009 ± 14 |
|  | 2:1 | 4 ± 2b | 1,056 ± 13 |
|  | 4:1 | 4 ± 2b | 1,120 ± 8 |
|  | 8:1 | 1 ± 1b | 400 ± 30 |
| CF Boiled | 1:1 | 20 ± 5b | — |
|  | 2:1 | 3 ± 2b | — |
|  | 4:1 | 1 ± 1b | — |
|  | 8:1 | 0 ± 0c | — |
| CF Frozen | 1:1 | 5 ± 3b | — |
|  | 2:1 | 3 ± 2b | — |
|  | 4:1 | 4 ± 3b | — |
|  | 8:1 | 2 ± 2b | — |

[a]Numbers followed by different letters differ at P = 0.05. Length measurements were taken at seven days.
[b]Each treatment was replicated nine times.
[c]Average number of nematodes in a 50-ul subsample from a 2500-ul sample. Means separated by t tests (Minitab).
[d]— = no measurements taken.

TABLE 8

Development of Nematode Reproduction Inhibiting Activity in CR-43 Cultures with Time

|  | Number of *C. elegans* (#/ml) | Reproduction Inhibition (%) |
|---|---|---|
| PDB Control | 63 ± 14 | 0 |
| Day Culture Filtrate Collected |  |  |
| 1 | 64 ± 14 | 0 |
| 2 | 55 ± 15 | 14 |
| 3 | 29 ± 19 | 55 |
| 4 | 25 ± 16 | 62 |
| 5 | 15 ± 8 | 77 |
| 6 | 5 ± 4 | 92 |
| 7 | 3 ± 4 | 96 |

EXAMPLE 9

Streptomyces dicklowii CR-43 Inhibits Nematode Egg Laying

Materials and Methods

Newly hatched *C. elegans* were placed in 2.5 ml *S. dicklowii* CR-43 culture filtrate (CF), obtained as described in Example 8, and 2.5–5 ml liver extract medium was added. The cultures were incubated at 22° C. for seven days. Adult *C. elegans* were examined under a light microscope at 100× magnification to determine if CF had any effect upon egg or gonad formation.

Results

Figure 3:
FIG. 3 depicts a female Caenorhabditis elegans nematode treated for six days with filtered culture medium from a *S. dicklowii* CR-43 culture. As illustrated, larvae are developing within the unlaid and unhatched eggs present in the female. Untreated female nematodes lay such eggs which then hatch before larvae develop. Reproduction is therefore inhibited in female nematodes treated with *S. dicklowii* culture medium.

Nematodes exposed to low levels of CF that did not affect growth (e.g. 1–2 parts CF to 1 part liver extract) underwent normal maturation, including normal formation of the vulva, vagina and the adult gonads. Under normal circumstances female nematodes lay eggs in the culture medium, the eggs hatch and larvae develop outside the uterus. However, observation of female nematodes cultured in even low levels of CF indicated that egg laying was significantly inhibited (P=0.01). Such inhibition resulted in nematode larvae developing within unlaid eggs (FIG. 3). Unlaid eggs were observed to occasionally hatch within the female, releasing larvae into the uterus. Further observation indicated that egg-laying inhibition was complete and that any small increase in nematode population was attributable to endotokia matricidia, i.e. larval hatching within the uterus resulting in the death of the female, and the occasional escape of young larvae from the dead nematode.

EXAMPLE 10

Characterization of the Egg Laying Inhibiting Factor from *Streptomyges dicklowii* CR-43

Materials and Methods

Culture filtrate (CF) was obtained from *S. dicklowii* cultures as in Example 8.

Molecular weight estimates of the active antinematodal fractions in CF were made by dialysis studies. CF from 7-day-old cultures were dialyzed against distilled water for 48 hr with three changes of water. Molecular weight cutoffs of the dialysis membranes were 6,000–8,000 daltons, and 12,000–14,000 daltons. Each dialysis level was tested three times. The efficacy of dialyzed and undialyzed CF was tested as described in Example 8.

CF from the time course study was examined by SDS gel electrophoresis to correlate the occurrence of a new protein in CF with antinematodal activity against *C. elegans*. Extracts were treated with SDS-mercaptoethanol and proteins separated on 7.6% polyacrylamide gels on a Hoefer Scientific SE600 vertical slab unit with discontinuous buffer, as described by Laemmli (1970 Nature 227: 680–685). Gels were stained with silver nitrate to enhance the sensitivity for detection of protein (Merril et al., 1980 Science 211: 1437–1438).

Results

Figure 4:
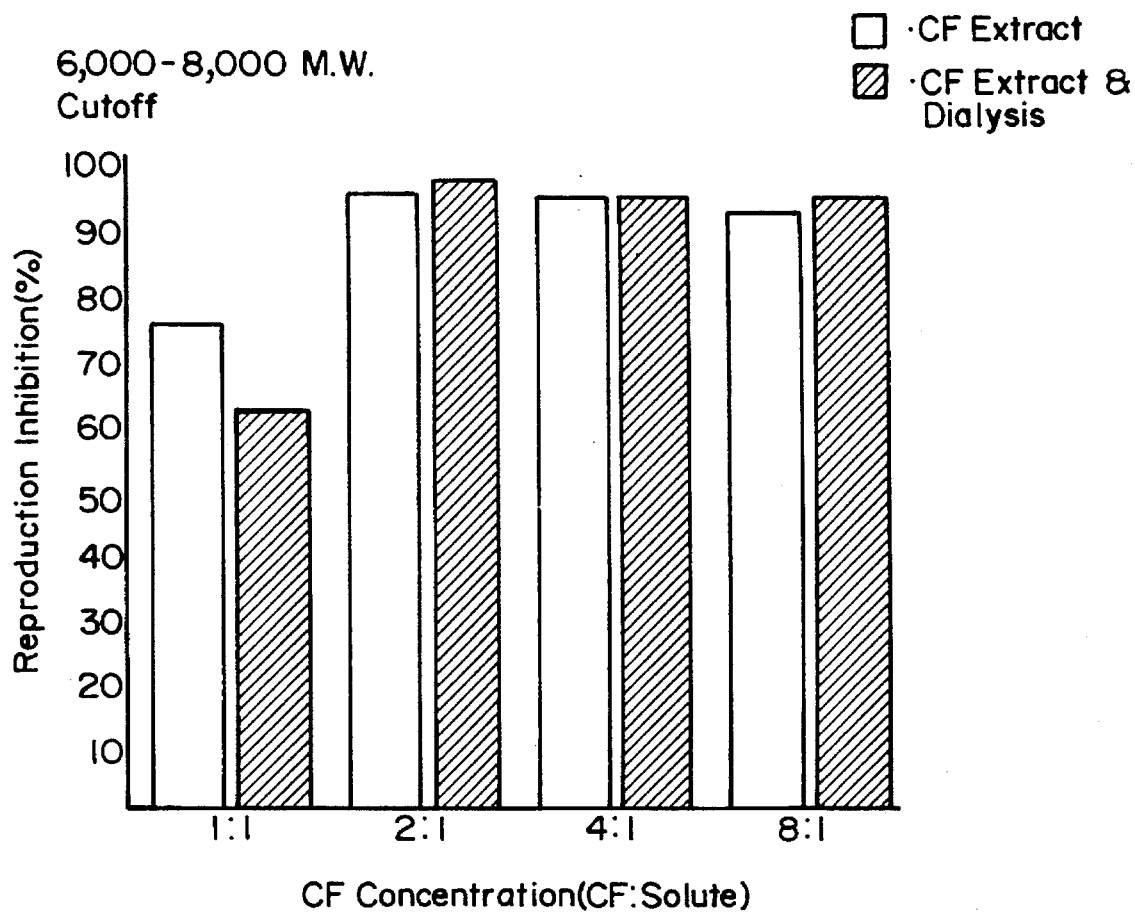
FIG. 4 depicts the % inhibition of nematode reproduction observed when *C. elegans* nematodes are maintained in undialyzed (open bar) and dialyzed (hatched bar) 1:1, 2:1, 4:1 and 8:1 (CF:liver extract medium) dilutions of culture filtrate (CF) from a *S. dicklowii* CR-43 culture. Dialysis was with a 6,000 to 8,000 daltons molecular weight cut-off membrane. Dialysis had little effect upon the % inhibition. Therefore, the reproduction inhibiting factors have a molecular weight which is greater than 6,000 to 8,000 daltons.
Figure 5:
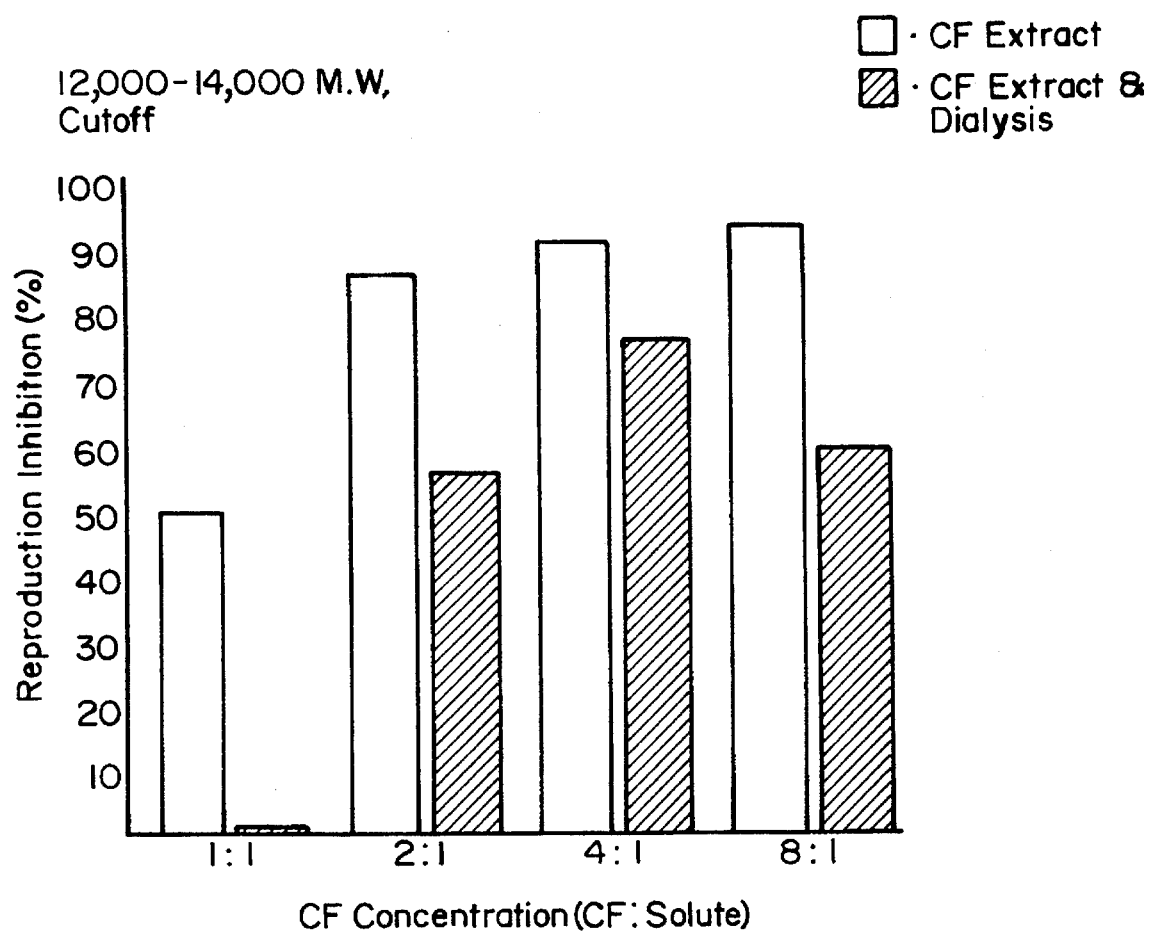
FIG. 5 depicts the % inhibition of nematode reproduction observed when *C. elegans* nematodes are maintained in undialyzed (open bar) and dialyzed (hatched bar) 1:1, 2:1, 4:1 and 8:1 (CF:liver extract medium) dilutions of culture filtrate (CF) from a *S. dicklowii* CR-43 culture. Dialysis was with a 12,000 to 14,000 daltons molecular weight cut-off membrane. Dialysis caused a partial reduction in the % inhibition of reproduction. Therefore, more than one *S. dicklowii* factor can cause reproduction inhibition and at least one of the reproduction inhibiting factors has a molecular weight which is about 12,000 to 14,000 daltons.

Dialysis against a membrane with a 6,000–8,000 daltons mol. wt. cutoff resulted only on a slight reduction in egg-laying capacity at the 1:1 dilation, indicating that the major constituents of CF responsible for inhibition of egg-laying were greater than 8,000 daltons molecular weight (FIG. 4). At the 2:1, 4:1, and 8:1 concentrations, there was no loss of egg-laying inhibition capacity, suggesting that concentration of the CF factors is of importance to the inhibition phenomenon. Dialysis against membranes with 12,000–14,000 daltons mol. wt. cutoffs resulted in a partial loss of egg-laying inhibition at all concentrations, providing evidence that two or more proteins present in CF were responsible for the observed antinematodal effect (FIG. 5). At 24 hr. CF showed no antinematodal activity against *C. elegans*; however, after three days of culture 55% egg-laying inhibition was observed and by seven days inhibition of egg laying was 96% (Table 8).

Figure 6:
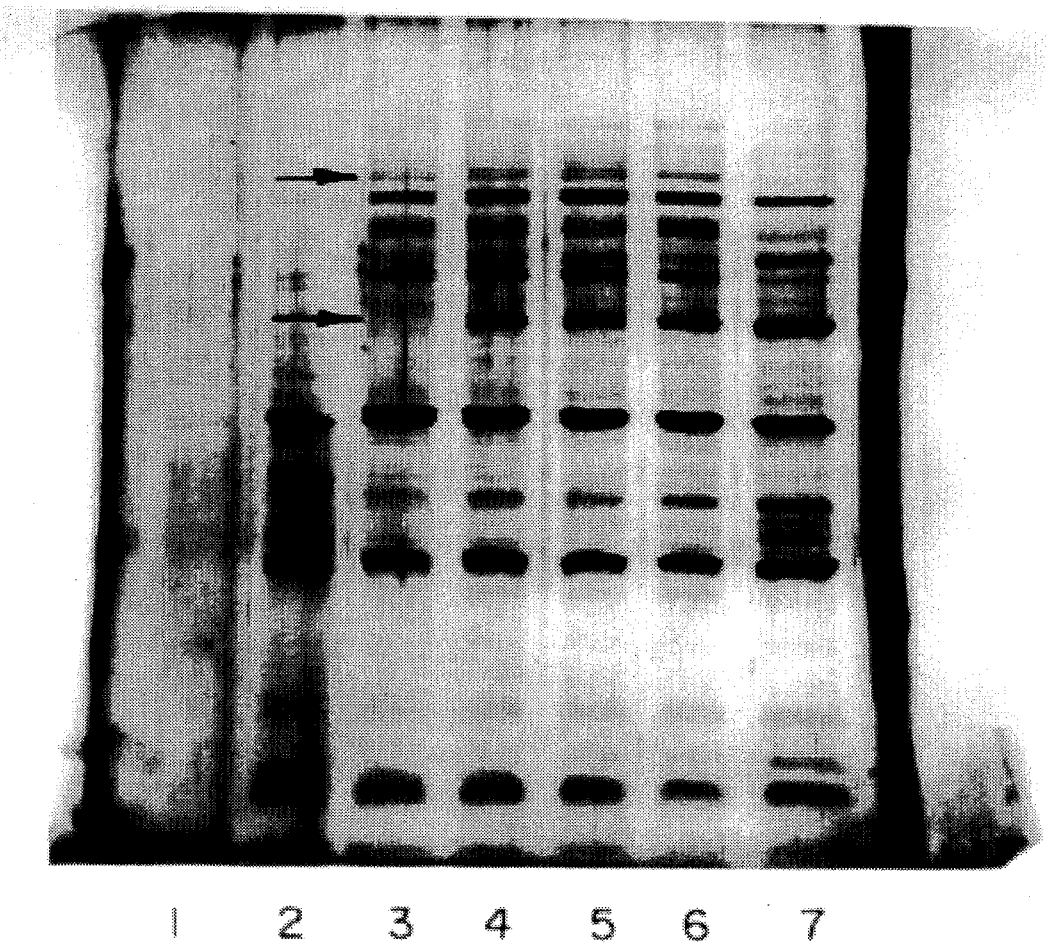
FIG. 6 depicts a sodium dodecyl sulfatepolyacrylamide gel electrophoretic pattern of proteins present in culture filtrates obtained daily from *S. dicklowii* cultures grown for 1–7 days. Lanes 1–7 contain culture filtrate proteins obtained on days 1–7, respectively.

SDS gel electrophoresis of CF at 24-hr. intervals for seven days indicated that a number of new proteins were visible coinciding with the presence of reproduction—inhibiting activity in CR-43 cultures. In particular, such new proteins had molecular weights between 55 and 160 kD and appeared by three days in CF (FIG. 6). These protein bands increased in intensity to seven days. These results and the dialysis experiments indicate that one or more proteins cause the observed antinematodal activity.

We claim:

1. A biologically pure *Streptomyces dicklowii* strain (ATCC 55274) wherein said *S. dicklowii* is active against nematodes and fungi.

2. A method for controlling or preventing diseases caused by nematodes comprising contacting soil, a plant or a seed with a nematocidally-effective amount of *Streptomyces dicklowii* (ATCC 55274) or with a nematocidally-effective amount of a medium from a Streptomyces dicklowii culture thereof.

3. The method of claim 2 wherein said nematodes are selected from the group consisting of Criconemella, Ditylenchus, Globodera, Helicotylenchus, Heterodera, Longidorus, Meloidogyne, Paratrichodorus, Pratylenchus, Radopholus, Rotylenchus, Rotylenchulus, Tylenchulus and Xiphinema.

4. The method of claim 2 wherein said nematocidally-effective amount of said strain comprises about $10^3$ to about $10^8$ colony forming units per gram of a carrier.

5. The method of claim 2 wherein from about 8 to about 10 pounds of a composition comprising said strain and a carrier is applied per acre of crop area, wherein said strain is at a concentration of about 10 to about $10^8$ colony forming units per gram of carrier.

6. The method of claim 2 wherein said soil is contacted by drenching said soil, said plant is contacted by spraying, dusting, or fertilizing said plant and said seed is contacted by coating said seed.

7. A method for controlling or preventing diseases caused by fungi which comprises contacting soil, a plant or a seed with a fungicidally-effective amount of *Streptomyces dicklowii* ATCC 55274).

8. The method of claim 7 wherein contacting comprises treating by pre-emergence or post-emergence treatment.

9. The method of claim 7 wherein said fungi are selected from the genera consisting of Rhizoctonia, Fusarium and Pythium.

10. The method of claim 7 wherein said plant is or said seed is for a field crop plant, vegetable plant, ornamental plant or fruit crop plant.

11. The method of claim 10 wherein said plant is a tomato, pepper, strawberry, orange, pineapple, cotton, plantain, banana, coffee, soybean or rice plant.

12. The method of claim 7 wherein said fungicidally-effective amount of said strain comprises about $10^3$ to about $10^8$ colony forming units per gram of carrier.

13. The method of claim 7 wherein from about 8 to about 10 pounds of a composition comprising said strain and a carrier is applied per acre of crop area, wherein said strain is at a concentration of about $10^3$ to about $10^8$ colony forming units per gram of carrier.

14. A biological control agent for control of nematode or fungal disease in plants comprising biologically pure *Streptomyces dicklowii* strain (ATCC 55274), and an agriculturally acceptable carrier.

15. The biological control agent of claim 14 wherein the amount of said *S. dicklowii* strain comprises about $10^3$ to about $10^8$ colony forming units per gram of said carrier.

16. The biological control agent of claim 14 wherein the amount of said *S. dicklowii* strain is about $10^5$ to about $10^6$ colony forming units per gram of said carrier.

17. The biological control agent of claim 14 wherein said agent is in a form selected from the group consisting of a seed coat, fertilizer, peat, prepackaged soil, drench, dust, spray, powder and liquid.

18. A method for inhibiting nematode egg laying which comprises contacting a female nematode population with an egg laying-inhibiting amount of *Streptomyces dicklowii* (ATCC 55274) or with an egg-laying-inhibiting amount of a culture medium thereof.

19. An agent for control of nematode or fungal disease in plants comprising cultured medium from *Streptomyces dicklowii* strain (ATCC 55274), and an agriculturally acceptable carrier.

20. A biologically pure culture of *Streptomyces dicklowii* designated by ATCC accession number 55274 or mutants thereof, wherein said mutants retain the nematocidal and fungicidal activity.

21. A method for controlling or preventing diseases caused by nematodes which comprises contacting soil, a plant or a seed with a nematocidaliy-effective amount of *Streptomyces dicklowii* or mutants thereof, wherein said mutants retain the nematocidal activity.

22. The method of claim 21 wherein said soil, plant or seed is contacted by coating said seed, drenching said soil, spraying said plant, dusting said plant or fertilizing said plant.

23. The method of claim 21 wherein said plant or said seed for a plant is selected from the group consisting of field crop plant, vegetable plant, ornamental plant and fruit crop plant.

24. The method of claim 23 wherein said plant or said seed for a plant is selected from the group consisting of tomato, pepper, strawberry, orange, pineapple, cotton, plantain, banana, coffee, soybean and rice plant.

25. A method for controlling or preventing diseases caused by nematodes which comprises contacting soil, a plant or a seed with a nematocidally-effective amount of a medium from a *Streptomyces dicklowii* culture.

26. The method of claim 25 wherein said nematocidally-effective amount of a medium is an undiluted *Streptomyces dicklowii* medium cultured for about 2 days to about 7 days.

27. The method of claim 25 wherein said medium is a *Streptomyces dicklowii* medium of strain (ATCC 55274) cultured for about 2 days to about 7 days which can be diluted with a liquid carrier.

28. A method for controlling or preventing diseases caused by fungi which comprises contacting soil, a plant or a seed with a fungicidally-effective amount of *Streptomyces dicklowii* or mutants thereof, wherein said mutants retain the fungicidal activity.

29. A biological control agent for control of nematodes or fungal disease in plants comprising an isolated and biologically pure *Streptomyces dicklowii* or mutants thereof, wherein said mutants retain the nematocidal or fungicidal activity, and an agriculturally acceptable carrier therefor.

30. A method for inhibiting nematode egg laying which comprises contacting a female nematode population with an egg laying-inhibiting amount of *Streptomyces dicklowii* or mutants thereof, wherein said mutants retain the nematocidal activity, or with an egg laying-inhibiting amount of a culture medium from said *Streptomyces dicklowii* strain.

31. A biological composition for control of nematode or fungal disease in plants comprising cultured medium from *Streptomyces dicklowii* or mutants thereof, wherein said mutants retain the nematocidal or fungicidal activity and an agriculturally acceptable carrier.

32. A biological composition for control of nematode or fungal disease in plants comprising a culture medium from *Streptomyces dicklowii* and an agriculturally acceptable carrier.

33. A biological composition comprising biologically pure culture of *Streptomyces dicklowii* and an agriculturally acceptable carrier.

34. A biologically pure culture of *Streptomyces dicklowii* strain (ATCC 55274) active against nematodes and fungi or mutants thereof, wherein said mutants retain the nematocidal and fungicidal activity.

35. A biologically pure culture of *Streptomyces dicklowii* designated by ATCC accession number 55274.

36. A biological composition comprising a biologically pure culture of *Streptomyces dicklowii* or mutants thereof wherein said mutants retain the nematocidal and fungicidal activity of said *Streptomyces dicklowii* and an agriculturally acceptable carrier.

* * * * *

UNITED STATES PATENT AND TRADEMARK OFFICE
CERTIFICATE OF CORRECTION

Page 1 of 2

PATENT NO. : 5,549,889
DATED : August 27, 1996
INVENTOR(S) : Bert M. Zuckerman, et. al.

It is certified that error appears in the above-indentified patent and that said Letters Patent is hereby corrected as shown below:

Column 1, line 5: "contniuation" should read --continuation--
Column 3, line 21: "beset" should read --best--.
Column 6, line 51: "after "include" delete -- - --.
Column 8, line 21: "pratylenchus" should read --Pratylenchus--.
Column 8, line 25: "M hapla" should read --M. hapla--.
Column 9, line 24: "preemergence" should read --pre-emergence--.
Column 9, line 30: "in,treating" should read --in treating--.

Column 11, line 58: "Streptomycetes." should read --Streptomyces--

Column 12, line 31: "Sytemic" should read --Systemic--

Column 13, lines 4 & 57: "nematicide" should read --nematocide--

Column 15, line 37: "nematicide" should read --nematocide--

Column 15, line 53: "NEMACUR " should read --NEMACUR® --

Column 19, line 36: "about.2" should read --about 2--

Column 20, line 55: "Streptomyges" should read --Streptomyces--

Column 21, line 60, Claim 5: "10" should read -- $10^3$ --.

Column 22, lines 1-2: after "dicklowii" insert --strain CR-43 (--

UNITED STATES PATENT AND TRADEMARK OFFICE
CERTIFICATE OF CORRECTION

PATENT NO. : 5,549,889
DATED : August 27, 1996
INVENTOR(S) : Bert M. Zuckerman, et. al.

It is certified that error appears in the above-indentified patent and that said Letters Patent is hereby corrected as shown below:

Column 22, line 51, Claim 21: "nematocidaliy" should read --nematocidally--
Column 24, line 10, Claim 33: after "comprising" insert --a--.

Signed and Sealed this

Twenty-third Day of September, 1997

Attest:

BRUCE LEHMAN

Attesting Officer

Commissioner of Patents and Trademarks